United States Patent
Redko et al.

(10) Patent No.: US 6,309,401 B1
(45) Date of Patent: Oct. 30, 2001

(54) APPARATUS AND METHOD FOR PERCUTANEOUS IMPLANT OF A PADDLE STYLE LEAD

(76) Inventors: Vladimir Redko, 6345 Westchester, Houston, TX (US) 77005; Kenneth M. Alo, 4512 Teas, Bellair, TX (US) 77401

( * ) Notice: Subject to any disclaimer, the term of this patent is extended or adjusted under 35 U.S.C. 154(b) by 0 days.

(21) Appl. No.: 09/302,694

(22) Filed: Apr. 30, 1999

(51) Int. Cl.$^7$ ................................................. A61B 17/34
(52) U.S. Cl. ......................................................... 606/185
(58) Field of Search ..................... 606/185, 15; 607/117, 607/116, 115; 604/105, 272, 273, 274, 181, 187, 264

(56) References Cited

U.S. PATENT DOCUMENTS

| | | |
|---|---|---|
| 4,141,365 | 2/1979 | Fischell et al. . |
| 4,143,658 * | 3/1979 | Rambosek et al. .................. 128/184 |
| 4,166,469 | 9/1979 | Littleford . |
| 4,512,351 * | 4/1985 | Pohndorf ............................. 607/117 |
| 4,660,571 | 4/1987 | Hess et al. . |
| 4,808,157 * | 2/1989 | Coombs ................................. 604/44 |
| 5,255,691 * | 10/1993 | Otten .................................. 607/117 |
| 5,669,882 | 9/1997 | Pyles . |
| 5,762,629 | 6/1998 | Kambin . |
| 5,843,146 | 12/1998 | Cross, Jr. . |
| 6,038,480 * | 3/2000 | Hrdicka et al. ....................... 607/116 |

FOREIGN PATENT DOCUMENTS

| | | |
|---|---|---|
| 2688407 | 9/1993 | (FR) . |
| WO9737720 | 10/1997 | (WO) . |

\* cited by examiner

*Primary Examiner*—Henry J. Recla
*Assistant Examiner*—Tan-Uyen T. Ho
(74) *Attorney, Agent, or Firm*—Banner & Witcoff, Ltd.

(57) ABSTRACT

A needle and method for introduction of a paddle style lead near a spinal column or other nervous system structures, central or peripheral, of a patient includes a body having a proximal end and a distal end, and a lumen with a continuous oblong cross section. The distal end of the body has an introducer portion where the top side of the introducer has an orifice to allow for protrusion of the paddle style lead from the lumen into the spinal column area or into or near other nervous system structures. The needle has a hub affixed to the proximal end of the body which is adapted to receive a stylet. The needle may also have a stylet that is inserted within the lumen. The introducer of the needle has a curvature extending from the bottom side toward the top side at the distal end and guides the introduction of the paddle style lead near the spinal column or other nervous system structures.

20 Claims, 4 Drawing Sheets

APPARATUS AND METHOD FOR PERCUTANEOUS IMPLANT OF A PADDLE STYLE LEAD

BACKGROUND OF THE INVENTION

1. Field of the Invention

This invention relates generally to a method and apparatus for the percutaneous introduction of a paddle style lead into nervous system structures of a patient including into the spinal canal or other nervous system structures, central or peripheral. More specifically, this invention relates to the percutaneous introduction of a paddle style lead into the spinal canal or other nervous system structures, central or peripheral, through a needle with an oblong cross section.

2. Description of Related Art

Spinal cord stimulation is used to treat a multitude of disorders including multiple sclerosis, spinal cord injury, cerebral palsy, amyotrophic lateral sclerosis, dystonia, torticollis and other neurological disorders. Spinal cord stimulation is also useful for treating pain including intractable malignant and nonmalignant pain. Neural stimulation electrodes and leads implanted in a patient in the epidural space of the spinal canal or other nervous system structures, central or peripheral, stimulate selected locations of the spinal canal or other nervous system structures for treatment of pain and various conditions.

Surgically implantable paddle style leads, or flat leads, and percutaneous insertable wire leads for the spinal canal have been in use for some time. These paddle style, or flat leads, and wire leads are used for electrical stimulation of neurons in the spinal canal. Two types of leads are generally used for spinal cord stimulation: 1) wire and 2) paddle.

Typically, a wire lead is introduced into the spinal canal using a needle and a stylet assembly. The needle and stylet are inserted into the spinal canal area between adjacent vertebrae until the tip of the needle and stylet are advanced into the epidural space of the spinal canal area. The stylet is withdrawn and a wire lead is inserted through the open area or lumen of the needle and into the epidural space to a selected location adjacent to the spinal cord. Some needle and stylet assemblies have a curved distal tip to facilitate introduction of the lead at an angle to the axis of the lumen portion of the needle. The needle typically has a side opening or orifice at its distal end for insertion of the lead into the selected location of the spinal canal. In some assemblies, the stylet may fill the entire lumen cavity including the side opening of the needle to prevent the collection of tissue in the lumen cavity during insertion of the needle. The stylet can also provide rigidity to the needle body for use during insertion.

Current needle technology requires that all leads be of a circular cross section in order to be placed through the lumen portion of the needle into the epidural space. Needles used for insertion of the wire leads typically have a circular cross section between 14 and 18 gauge.

The paddle style or flat leads are generally rectangular shaped flat paddles that must be surgically implanted. To introduce a paddle style lead into the epidural space percutaneously using needle insertion, the paddle lead must be rolled to a circular shape to slide through the typical circular cross section needle. The method of rolling the paddle lead and inserting through a needle and unrolling the paddle style lead has not been perfected for use. The only way to insert a paddle style lead is by a surgical procedure known as a laminotomy, a laminectomy, or similar surgical procedure. Because the paddle style lead must be surgically implanted, anesthesiologists may not perform the procedure.

Accordingly, there remains a need in the art for a non-surgical method of inserting a paddle style or flat lead into the spinal canal area.

SUMMARY OF INVENTION

The present invention recognizes and provides a solution to the problems associated with the percutaneous introduction of paddle style leads. The invention provides a unique needle for percutaneous insertion of a paddle style lead into the spinal canal area or into other nervous system structures, central or peripheral. Briefly, the present invention comprises a needle for percutaneous insertion having a lumen with an oblong cross section sized to receive a paddle style lead.

Accordingly, an object of the present invention is to provide an apparatus for percutaneous insertion of paddle style leads that may be utilized by both surgeons and anesthesiologists. Current needles used for introduction of leads for electrical stimulation have a round cross section. Paddle style leads cannot be inserted through these needles. The paddle style lead must be inserted by a surgeon performing a laminotomy, a laminectomy or similar surgical procedure where the surgeon cuts open the tissue and then slides the lead into the proper position. This novel invention uses a needle having a lumen with an oblong cross section. A flat, paddle style lead based on current lead technology is passed through the oblong cross section of the lumen in this needle for introduction into the spinal canal area or other nervous system structures, central or peripheral. This invention allows for percutaneous insertion through a needle without performing the above mentioned surgical procedures.

Another object of this invention is to provide a less traumatic procedure for patients during the implantation of paddle style leads for treatment. Surgical introduction of leads for electrical stimulation is traumatic for patients. Insertion of leads for electrical stimulation utilizing an oblong needle that is inserted near the spinal column or other nervous system structures, central or peripheral, is less traumatic for patients than surgery where the surgeon must cut the tissue open and then slide the lead into the proper position.

The full range of objects, advantages, and features of the invention are only appreciated by a full reading of this specification and a full understanding of the invention. Therefore, to complete this specification, a detailed description of the invention and the preferred embodiments follow, after a brief description of the drawing wherein additional objects, advantages and features of the invention are disclosed.

BRIEF DESCRIPTION OF THE DRAWINGS

A preferred embodiment of the invention is illustrated in the drawings, wherein like reference numerals refer to like elements in the various views, and wherein.

DESCRIPTION OF THE PREFERRED EMBODIMENTS

Figure 1:
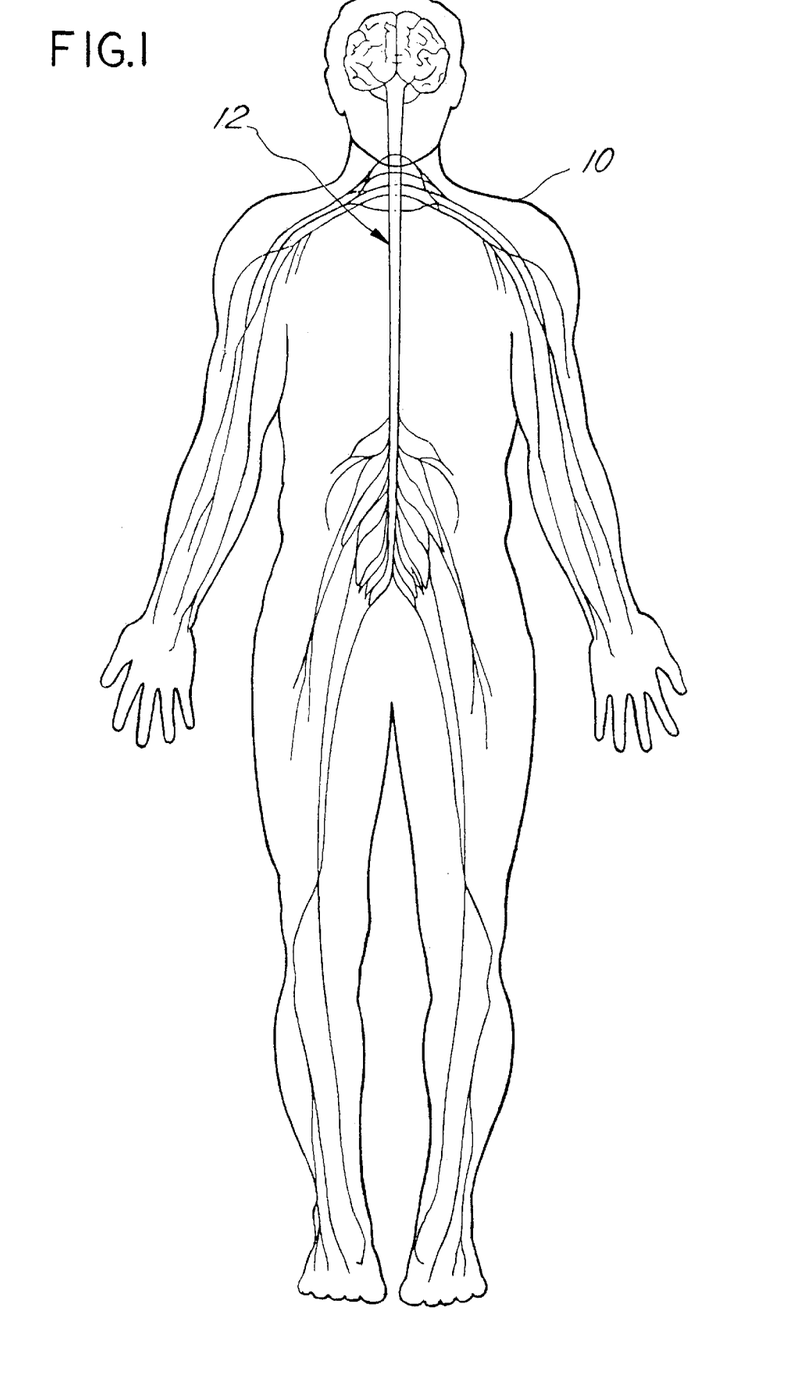
FIG. 1 is a perspective representation in partial cross section of the human body nervous system.
Figure 2:
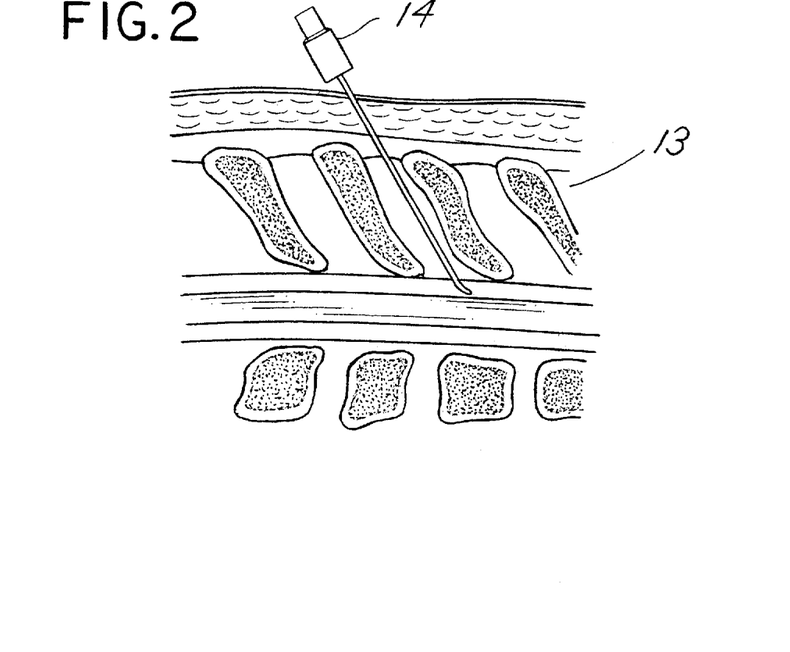
FIG. 2 is a perspective representation in partial cross section of the introduction of the assembled needle within the spinal area.

In the drawings, FIGS. 3–6 illustrate a preferred embodiment of a needle 15 and stylet 45 for use in the procedure for introducing a paddle style lead 55 within the spinal column area 13 as depicted in FIG. 2. The partial cross section of the outline of a human body 10 showing the nervous system including the spinal column 12 is depicted in FIG. 1. The method and apparatus of this invention can be used for the introduction of a paddle style lead 55 into the spinal column area 13 of the nervous system or into or near other nervous system structures, central or peripheral, such as intracranial nervous system structures or peripheral nerves.

Referring to FIG. 2, the assembled needle and stylet 14 are further depicted in relation to the spinal area 13. Needle assembly 14 is inserted into the spinal column area 13 in a fashion generally known in the art. In accordance with the novel improvement of the present invention, lumen 25 of the needle 15 has an oblong cross section sized to insert a paddle style lead and has a curve at the distal end 35 of the needle 15.

Figure 3:
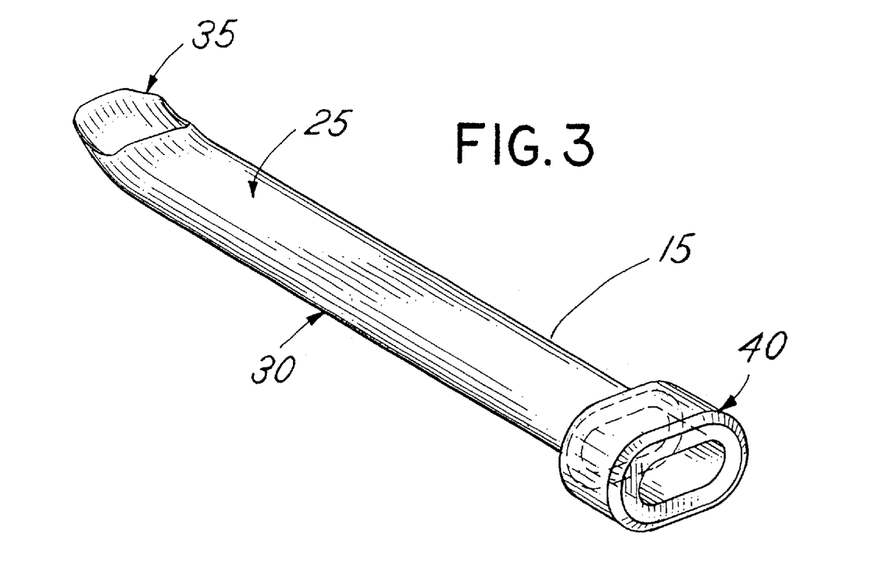
FIG. 3 is a perspective view of the preferred needle of the present invention.

Turning now to FIG. 3, a preferred embodiment of the needle 15 for percutaneous implant of a paddle style lead is depicted in perspective view. The needle 15 comprises a body 30 having a proximal end 40 and a distal end 35 and an inside lumen 25. The lumen 25 has an oblong cross section. The oblong cross section of the lumen 25 is adapted to receive a stylet 45 and a paddle style lead 55. The cross section of the lumen 25 is such that the width is greater than the height. A typical width for the lumen 25 cavity to receive a paddle style lead 55 is 2.5 mm to 12 mm (0.1" to 0.5") with a height of 1.4 mm to 2.0 mm (0.055" to 0.079"). The needle 15 is preferably made of stainless steel or other suitable materials. The needle 15 may also be adapted to insert multiple wire leads. Advantageously, the present invention allows a paddle lead to be inserted percutaneously without requiring the lead to be rolled/contorted to fit the geometry of the needle lumen.

Figure 4:
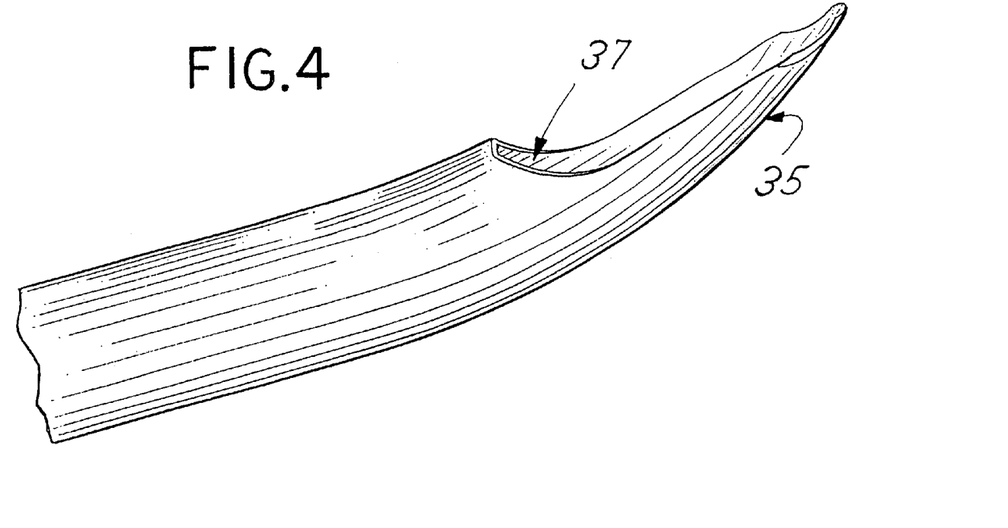
FIG. 4 is a perspective view of the preferred curved tip of the introducer portion of the needle of the present invention.

The needle 15 is further defined by an introducer portion 35 at the body 30 distal end. Referring to FIG. 4, the introducer portion 35 having a top side and a bottom side is shaped to allow for penetration of a patient's skin and other tissue. Typically, an epidural, Tuohy or modified Tuohy needle may be used. The top side of the introducer portion 35 has an orifice 37 to allow the paddle style lead 55 to exit the lumen 25 of the needle 15 within the spinal column area 13 after insertion of the needle 15. Those in the art will also know that the introducer portion 35 may have the orifice at the distal end perpendicular to the lumen 25. The preferred embodiment of the needle 15 has an introducer 35 with a curvature. The curvature extends from the bottom side of the introducer 35 to the top side of the introducer 35 to facilitate and guide the paddle style lead 55 during insertion. As preferred, the radius of curvature for the introducer 35 is approximately 0.9". Those skilled in the art will appreciate that any other curvature may be used and still be considered within the scope of the present invention.

Figure 5:
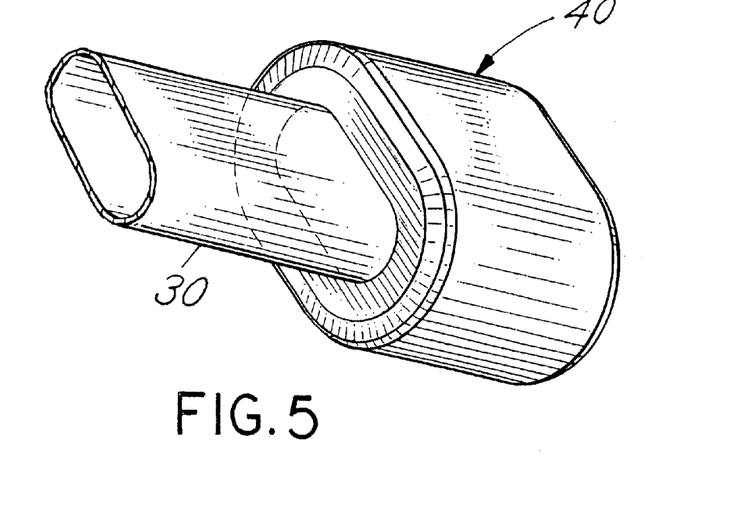
FIG. 5 is a perspective view of the preferred hub of the needle of the present invention.
Figure 8:
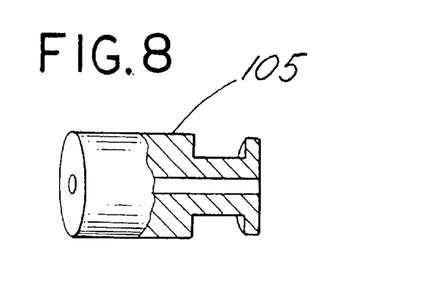
FIG. 8 is a partial cross section perspective view of a Luer lock.
Figure 9:
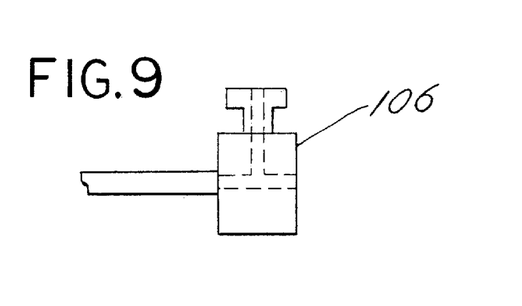
FIG. 9 is a perspective view of an alternative Luer lock.

Referring to FIG. 5, the body 30 proximal end is comprised of a hub 40. The hub 40 is affixed to the proximal end of the body 30 and allows the needle 15 to be grasped. Additionally, the hub 40 provides an interface between the needle 15 and the stylet 45 during insertion. Referring to FIG. 8, an alternative embodiment of the hub 40 comprises a Luer lock 105 to allow for extracting or inserting fluids or for allowing the physician to use the loss of resistance method for identifying the epidural space. Referring to FIG. 9, an alternative embodiment of the Luer lock 106 is depicted.

Figure 6:
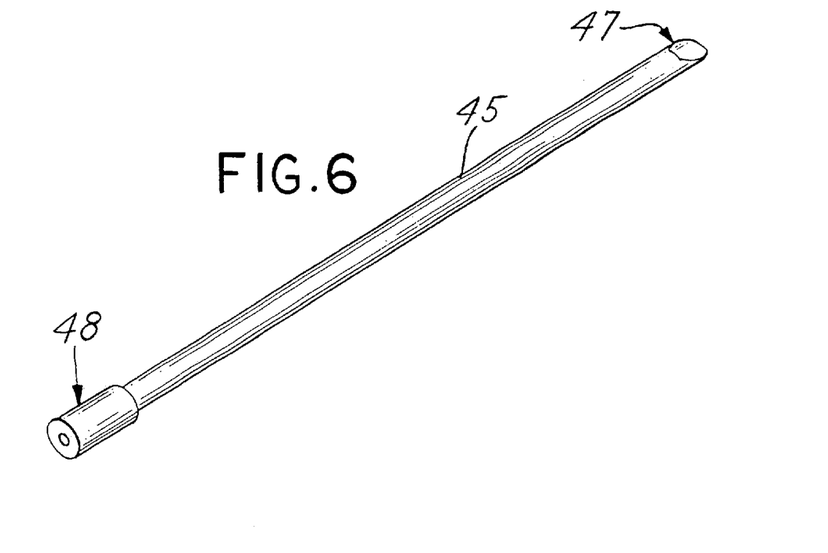
FIG. 6 is a perspective view of the preferred stylet of the present invention.

Turning to now to FIG. 6, it illustrates a perspective view of the stylet 45 having a proximal end that is adapted to mate with the needle hub 40. The stylet 45 may be constructed of stainless steel having a length nearly equivalent to the length of the body 30 of the needle 15. The stylet 45 has a distal tip 47 shaped for matching with the orifice 37 of the introducer 35 of the needle 15. A handle end 48 is affixed to a proximal end of the stylet 45. In the preferred embodiment, the stylet 45 fills the entire orifice 37 of the introducer 35 to prevent any skin or other tissue from entering the lumen 25 during insertion within the patient.

Figure 7:
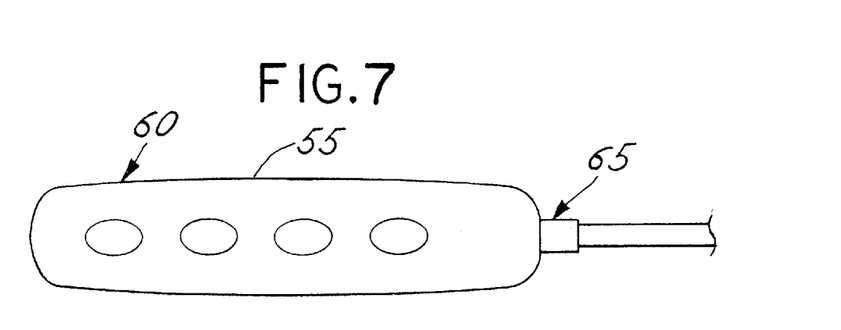
FIG. 7 is a top view of a paddle style lead.

FIG. 7 illustrates a top view of a paddle style lead 55 for electrical stimulation. The paddle style lead 55 is sized such that the width of the paddle style lead 55 is less than the width of the lumen 25 and such that tie height of the paddle style lead 55 is less than the height of the lumen 25. The paddle style lead 55 has a lead body 60 and transition area 65. Once inserted in the spinal column area 13, the paddle style lead 55 remains in position and wire leads extend out of the spinal canal typically to a signal generator. The described sizing allows the paddle style lead 55 to be inserted through the lumen 25 into the spinal column area 13 after the needle 15 is inserted in a predetermined position.

The description of the apparatus of this invention is not intended to be limiting but is merely illustrative of the preferred embodiment of this invention. Those of ordinary skill in the art will recognize that modifications can be made to the needle and paddle style leads described herein without departure from the true spirit and scope of the invention.

The true spirit and scope of the inventions of this specification are best defined by the appended claims, to be interpreted in light of the foregoing specification. Other apparatus which incorporate modifications or changes to that which has been described herein are equally included within the scope of the following claims and equivalents thereof. Therefore, to particularly point out and distinctly claim the subject matter regarded as the invention, the following claims conclude this specification.

We claim:

1. A needle for introduction of a paddle style lead near a spinal column or into or near nervous system structures of a patient, comprising, in combination:

a body having a proximal end and a distal end, a lumen having a continuous oblong cross section defined by a solid outer wall, and a stylet having a handle end at a proximal end, a solid body extending from the proximal end to the distal end and adapted to be inserted within the lumen.

2. The needle of claim 1, wherein the distal end is further defined by an introducer portion having a top side and a bottom side, the top side of the introducer having an orifice to allow for protrusion of the paddle style lead from the lumen.

3. The needle of claim 2, wherein the introducer has a curvature extending from the bottom side toward the top side at the distal end to provide a guide for introduction of the paddle style lead near the spinal column or into or near nervous system structures.

4. The needle of claim 3, wherein the stylet fills in the top side of the introducer element preventing tissue from entering the lumen during insertion.

5. The needle of claim 1, wherein the body is further defined by a hub affixed to the proximal end of the body adapted to receive the stylet.

6. The needle of claim 1, wherein the hub is a Luer lock.

7. The needle of claim 1, wherein the stylet fills in the distal end of the body preventing tissue from entering the lumen during insertion.

8. A needle for introduction of a paddle style lead near a spinal column or into or near nervous system structures of a patient, comprising, in combination:
   a body having a proximal end and a distal end,
   a lumen having a continuous oblong cross section defined by a solid outer wall,
   the paddle style lead having a lead body and wires connected at a transition area adapted to be inserted through the oblong cross section of the lumen.

9. The needle of claim 8, wherein the combination further comprises at least two wire leads adapted to be inserted through the oblong cross section of the lumen.

10. A needle for introduction of a paddle style lead near a spinal column or into or near nervous system structures of a patient, comprising, in combination:
    a body having a proximal end and a distal end,
    a lumen having a continuous oblong cross section defined by a solid outer wall, wherein the distal end is further defined by an introducer portion having a top side and a bottom side,
    the top side of the introducer portion having an orifice to allow for protrusion of the paddle style lead from the lumen;
    a hub affixed to the proximal end of the body adapted to receive a stylet, and
    the stylet having a handle end at a proximal end, a solid body extending from the proximal end to the distal end and adapted to be inserted within the lumen.

11. The needle of claim 10, wherein the introducer has a curvature extending from the bottom side toward the top side at the distal end to provide a guide for introduction of the paddle style lead near the spinal column or into or near nervous system structures.

12. The needle of claim 10, wherein the hub is a Luer lock.

13. The needle of claim 10, wherein the stylet fills in the top side of the introducer element preventing tissue from entering the lumen during insertion.

14. A needle for introduction of a paddle style lead near a spinal column or into or near nervous system sues of a patient comprising, in combination:
    a body having a proximal end and a distal end,
    a lumen having a continuous oblong cross section defined by a solid outer wall, wherein the distal end is further defined by an introducer portion having a top side and a bottom side,
    the top side of the introducer portion having an orifice to allow for protrusion of the paddle style lead from the lumen,
    a hub affixed to the proximal end of the body adapted to receive a stylet, and
    the paddle style lead having a lead body and wires connected at a transition area adapted to be inserted through the oblong cross section of the lumen.

15. The needle of claim 14, wherein the combination further comprises at least two wire leads adapted to be inserted through the oblong cross section of the lumen.

16. A needle for introduction of a paddle style lead near a spinal column or into or near nervous system structures of a patient, comprising, in combination:
    a body having a proximal end and a distal end, and a lumen having a continuous oblong cross section, wherein the distal end is further defined by an introducer portion having a top side and a bottom side, the top side of the introducer having an orifice to allow for protrusion of the paddle style lead from the lumen, the introducer having a curvature extending from the bottom side toward the top side at the distal end to provide a guide for introduction of the paddle style lead near the spinal column or into or near nervous system structures;
    a hub affixed to the proximal end of the body adapted to receive a stylet; and
    a stylet having a handle end at a proximal end and adapted to be insertable within the lumen, wherein the stylet fills in the top side of the introducer element preventing tissue from entering the lumen during insertion.

17. The needle of claim 16, wherein the combination further comprises a paddle style lead having a lead body and wires connected at a transition area adapted to be inserted through the oblong cross section of the lumen.

18. The needle of claim 16, wherein the combination further comprises at least two wire leads adapted to be inserted through the oblong cross section of the lumen.

19. A needle for introduction of a paddle style lead near a spinal column or into or near nervous system structures of a patient, comprising, in combination:
    a body having a primal end and a distal end, and a lumen having a continuous oblong cross section defined by a solid outer wall, wherein the distal end is further defined by an introducer portion having a top side and a bottom side, the top side of the introducer having an orifice to allow for protrusion of the paddle style lead from the lumen, the introducer having a curvature extending from the bottom side toward the top side at the distal end to provide a guide for introduction of the paddle style lead near the spinal column or into or near nervous system structures;
    a hub affixed to the proximal end of the body adapted to receive a stylet;
    a stylet having a handle end at a proximal end and adapted to be inserted within the lumen, wherein the stylet fills in the top side of the introducer element preventing tissue from entering the lumen during insertion; and
    the paddle style lead having a lead body and wires connected at a transition area adapted to be inserted through the oblong cross section of the lumen.

20. A needle for introduction of a paddle style lead near a spinal column or into or near nervous system structures of a patient, comprising, in combination;
    a body having a proximal end and a distal end, and a lumen having a continuous oblong cross section defined by a solid outer wall wherein the distal end is further defined by an introducer portion having a top side and a bottom side, the top side of the introducer having an orifice to allow for protrusion of the paddle style lead from the lumen, the introducer having a curvature extending from the bottom side toward the, top side at the distal end to provide a guide for introduction of the paddle style lead near the spinal column or into or near nervous system structures;
    a hub affixed to the proximal end of the body adapted to receive a stylet;

a stylet having a handle end at a proximal end and adapted to be insertable within the lumen, wherein the stylet fills in the top side of the introducer element preventing tissue from entering the lumen during insertion; and at least two wire leads adapted to be inserted through the oblong cross section of the lumen.

* * * * *

UNITED STATES PATENT AND TRADEMARK OFFICE
CERTIFICATE OF CORRECTION

PATENT NO. : 6,309,401 B1
APPLICATION NO. : 09/302694
DATED : October 30, 2001
INVENTOR(S) : Vladimir Redko et al.

Page 1 of 1

It is certified that error appears in the above-identified patent and that said Letters Patent is hereby corrected as shown below:

Column 5,
Line 53, change "a spinal column or into or near nervous system sues of a" to
-- a spinal column or into or near nervous system structures of a --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO. : 6,309,401 B1 Page 1 of 1
APPLICATION NO. : 09/302694
DATED : October 30, 2001
INVENTOR(S) : Redko et al.

It is certified that error appears in the above-identified patent and that said Letters Patent is hereby corrected as shown below:

Column 5, Line 10, please change:

--6. The needle of claim 1, wherein the hub is a Luer lock.-- to

--6. The needle of claim 5, wherein the hub is a Luer lock.--

Signed and Sealed this

Fifteenth Day of August, 2006

JON W. DUDAS
*Director of the United States Patent and Trademark Office*